United States Patent [19]
Abys et al.

[11] Patent Number: 6,139,711
[45] Date of Patent: Oct. 31, 2000

[54] HYDRODYNAMICALLY CONTROLLED HULL CELL AND METHOD OF USE

[75] Inventors: Joseph Anthony Abys, Warren; Joseph John Maisano, Branchburg, both of N.J.; Lars Goran Holmbom, Linkoping, Sweden

[73] Assignee: Lucent Technologies Inc., Murray Hill, N.J.

[21] Appl. No.: 09/251,547

[22] Filed: Feb. 17, 1999

[51] Int. Cl.[7] .................................................. C25D 21/12
[52] U.S. Cl. .............................. 205/81; 205/96; 205/134; 205/137; 204/212; 204/DIG. 7
[58] Field of Search .................................. 204/21, DIG. 7, 204/272; 205/134, 137, 150, 96, 81

[56] References Cited

U.S. PATENT DOCUMENTS

5,413,692  5/1995  Abys et al. ............................. 204/434

*Primary Examiner*—Kathryn Gorgos
*Assistant Examiner*—Thomas H. Parsons
*Attorney, Agent, or Firm*—Schnader Harrison Segal & Lewis, LLP

[57] ABSTRACT

An apparatus for measuring the throwing power of electroplating solutions which provides a nearly linear current density distribution across the panel. The apparatus includes a cylindrical body adapted for rotation about a longitudinal axis thereof, a cylindrical cathode arranged coaxially about a central portion of the cylindrical body, an anode coaxially positioned at a lower end portion of the cylindrical body, a conical shield coaxially arranged around an upper end portion of the cathode; and an annular disk-baffle coaxially arranged around a lower end portion of the cathode. The conical shield and the disk-baffle provide a substantially linear current distribution over the cathode. In another aspect, the invention includes a method for measuring the throwing power of an electrolyte comprising using the instrument of the invention to analyze the variation in the appearance of an electrodeposit over a wide range of current densities along test panel by providing a nearly linear current density distribution across the panel in order to determine optimal electroplating conditions.

8 Claims, 9 Drawing Sheets

HYDRODYNAMICALLY CONTROLLED HULL CELL AND METHOD OF USE

BACKGROUND OF THE INVENTION

This invention relates to apparatus and a method for measuring the throwing power of electroplating solutions, particularly to an improved hydrodynamically controlled hull cell which provides a nearly linear current density distribution across a test panel.

DESCRIPTION OF THE RELATED ART

Electroplating process control systems such as the Hull Cell, described in U.S. Pat. No. 2,149,344, incorporated herein by reference, and the Hydrodynamically Controlled Hull Cell (HCHC), described in U.S. Pat. No. 5,275,711, incorporated herein by reference, provide useful information for research, development and production applications. Using these control systems, a wide range of current densities can be evaluated in a single experiment. These systems are commonly used for maintenance of plating solutions to insure continuous production of satisfactory deposits and for the development of new electrolytes. There are, however, two main problems associated with the use of the standard Hull Cell. First, the standard Hull Cell produces uncontrolled and non-uniform transport of matter during a test. This problem has been eliminated with the introduction of the conventional HCHC which provides information with reproducible and well established transport of matter.

The second problem associated with the use of both the standard Hull Cell and the conventional HCHC is the inadequate current distribution profile across the test panel. The wide current density and the logarithmic dependence of the range obtained with standard equipment makes it difficult to identify qualitative changes for specific current densities. The typical current distribution curve for electroplating solutions attainable with standard Hull Cell equipment is similar to the primary current distribution function. It is a logarithmic curve of the type $C_1-C_2 \log L$, where L is the variable length of the test panel. Use of data from tests having this current distribution profile is limited since in the low current density range, approximately 40% of the panel, the current density varies little with the horizontal panel distance. Similarly, in the high current density range, the horizontal distance remains relatively constant while the current density increases significantly. In both the cases, the results are difficult to interpret and valuable practical information is lost.

Current distribution remains a common limitation to both standard Hull Cell systems and to conventional HCHC systems. Therefore, a need exists iLo optimize the current distribution across an HCHC test panel.

BRIEF DESCRIPTION OF THE INVENTION

The present invention is directed to an apparatus for measuring the throwing power of electroplating solutions which provides a nearly linear current density distribution across the panel. The apparatus is easy to use and gives reproducible measurements. The invention permits the study of throwing power of electroplating solutions over a wide range of hydrodynamic conditions.

An instrument having features of the present invention comprises a cylindrical body adapted for rotation about a longitudinal axis thereof, a cylindrical cathode arranged coaxially about a central portion of the cylindrical body, an anode coaxially positioned at a lower end portion of the cylindrical body, a conical shield coaxially arranged around an upper end portion of the cathode; and an annular disk-baffle coaxially arranged around a lower end portion of the cathode. The conical shield and the disk-baffle provide a substantially linear current distribution over the cathode.

In another aspect, the invention comprises a method for testing an electroplating solution comprising attaching a test panel to the instrument of the invention, electrolytically cleaning said test panel, applying a current to said instrument, setting a desired rate of rotation of said cylindrical body, immersing said instrument in an electroplating solution such that approximately 50% of said conical shield is immersed, rotating said cylindrical body, removing said instrument from said electroplating solution and evaluating said test panel for thickness distribution.

These and other features, aspects, and advantages of the present invention will become better understood with regard to the following description, appended claims and accompanying drawings.

DETAILED DESCRIPTION OF THE INVENTION

The hydrodynamically controlled hull cell apparatus of the present invention, hereinafter referred to as the L-Cell, can be used to analyze the variation in the appearance of an electrodeposit over a wide range of current densities along a cathode surface in order to determine optimal electroplating conditions. The L-Cell provides a substantially linear current density distribution across a test panel. Substantially linear current density distribution as used herein refers to a distribution of current having regression coefficient of at least about 0.9 when correlating the distance from the anode with current density.

In a conventional HCHC electrode system, one of the design and operation goals is to achieve maximum similarity with the standard Hull Cell in terms of the theoretical current density distribution. The HCHC utilizes a rotating cylinder to control the mass transfer conditions accurately while applying a current density range typical of a conventional Hull Cell. The design elements of an HCHC system such as the HCHC electrode and the container play an important role in simulating the standard Hull Cell current density distribution. In the present invention the design elements have been modified to develop a substantially linear current density distribution across the test panel.

Figure 1A:
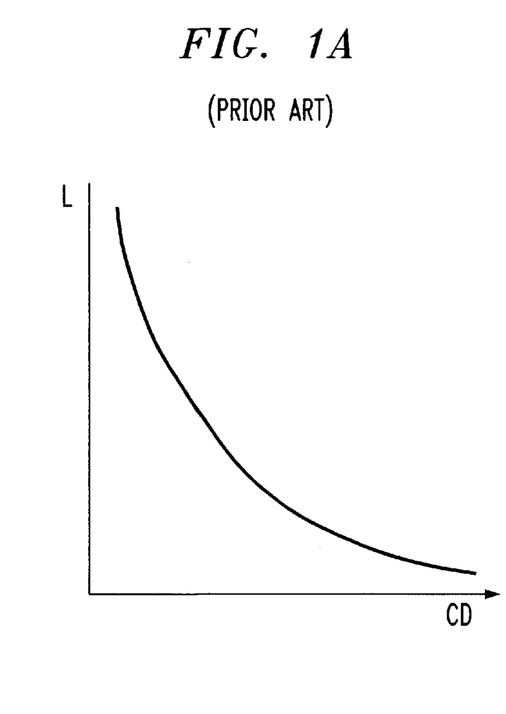
FIG. 1A is a plot of the typical current density (CD) distribution over the length (L) of the cathode of a hydrodynamically controlled hull cell of the prior art.

A plot of the current density (CD) distribution over the length (L) of the cathode of a conventional HCHC electrode of the prior art is shown in FIG. 1A. This geometry provides a range of current densities along the cathode. By placing the anode at one end of the cathode, the current density is the highest at the end closest to the anode. The current density tapers down as you move along the cathode away from the anode. The end of the cathode furthest from the anode is the lower current density end.

Figure 1B:
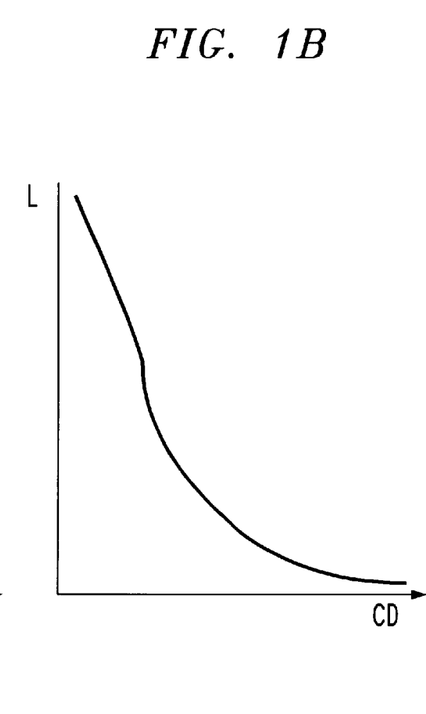
FIG. 1B is a plot of the current density (CD) distribution over the length (L) of the cathode of a hydrodynamically controlled hull cell with the introduction of a conical shield.

To achieve a substantially linear current density distribution as a function of distance along the cathode requires a steeper current change with the cathode length at the low current density end so that the tapering effect is minimized. This beneficial effect is achieved by introduction of a conical shield in the area of low current density. As shown in the plot of current density (CD) over the length (L) of the cathode in FIG. 1B, by introducing a conical shield to the low current density end of the conventional HCHC electrode, the taper effect of the current density distribution is significantly reduced.

Figure 1C:
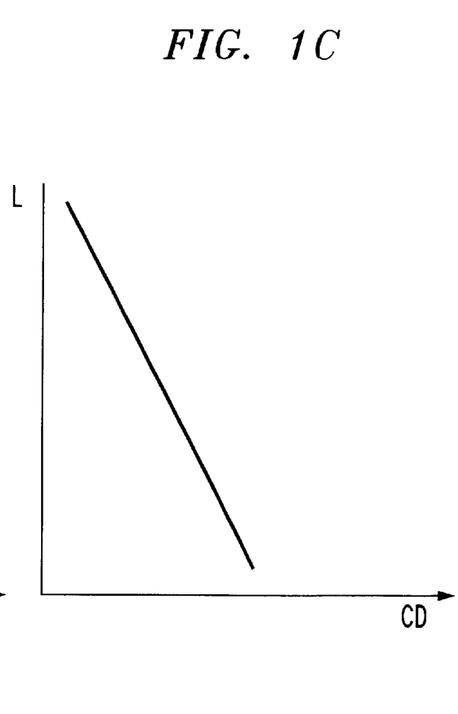
FIG. 1C is a plot of the current density (CD) distribution over the length (L) of the cathode of one embodiment of the present invention.

In the high current density end, the current variation with the cathode length must be significantly reduced to achieve a substantially linear relationship with the cathode length. The sharp increase in the current at the high current density end of the cathode is reduced by the introduction of a disk-baffle perpendicular to the plane of the cathode cylinder at the high current density end of the cathode. FIG. 1C illustrates the effect on current density (CD) distribution over the length (L) of the cathode from the introduction of both a conical shield in the area of low current density and a disk baffle in the area of high current density.

Figure 2:
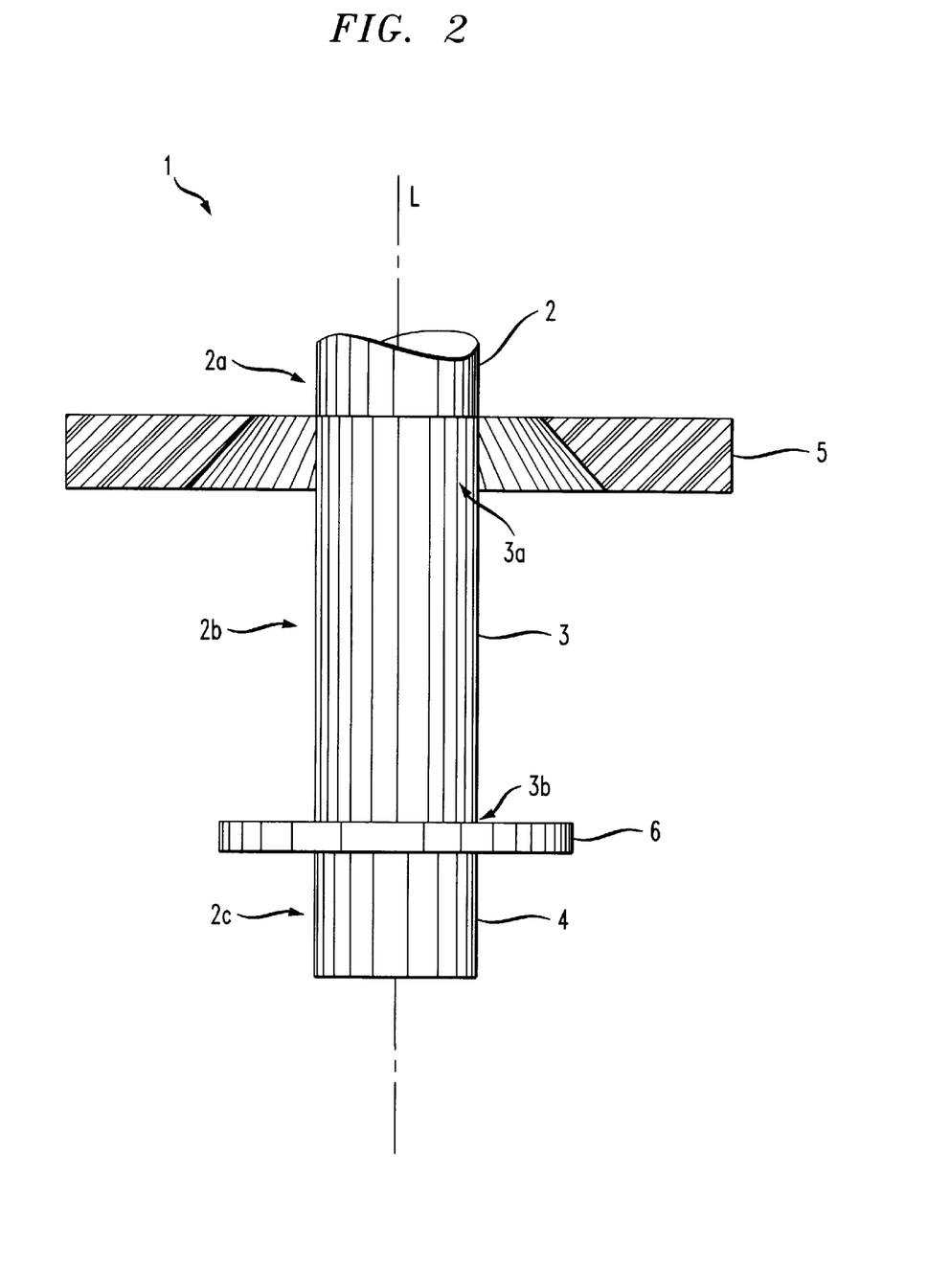
FIG. 2 is a schematic representation of one embodiment of the present invention.

One embodiment of the L-Cell of the present invention is shown in FIG. 2. The L-Cell 1 includes a cylindrical body 2 adapted for rotation about a longitudinal axis L. The cylindrical body 2 has an upper end portion 2a, a central portion 2b and a lower end portion 2c. A cylindrical cathode 3 is arranged coaxially about the central portion 2b of said cylindrical body 2. The cathode 3 has an upper end portion 3a, a lower end portion 3b and an outer surface. An anode 4 is coaxially positioned at the lower end portion 2c of the cylindrical body 2. A conical shield 5 is coaxially arranged around the upper end portion 3a of the cathode 3. An annular disk-baffle 6 is coaxially arranged around the lower end portion of the cathode 3. The conical shield 5 (shown in a cross-sectional view) and the disk-baffle 6 provides a substantially linear current distribution along the length of the cathode 3.

The cylindrical body 2 is preferably an elongated cylinder of a suitable electrically non-conducting material which is not adversely affected by the plating reaction and is non-contaminating with respect to electroplating solutions. Suitable material for the cylinder body 2 include such insulating materials as epoxy, polyethylene, polypropylene, polyvinyl chloride, glass and other materials possessing the above qualities. For ideal hydrodynamic uniformity, it is preferable that the cylindrical body 2 have a diameter of about 0.75 inch.

The anode 4 and the cathode 3 are made of metal which also is non-reacting and non-contaminating with respect to plating solutions. Stainless steels and refractory metals such as titanium, niobium and tantalum are some of the materials suitable for this purpose. Current to the anode 4 and the cathode 3 may be provided using slip ring electrode contacts and insulated leads, or by any method known in the art.

The conical shield 5 and the annular disk baffle 6 are insulators which modify the electric field between cathode 3 and anode 4. It is preferable that conical shield 5 and disk baffle 6 do not substantially influence the hydrodynamics of the apparatus so as to disturb the substantially linear current density distribution across the cathode 3.

Figure 3:
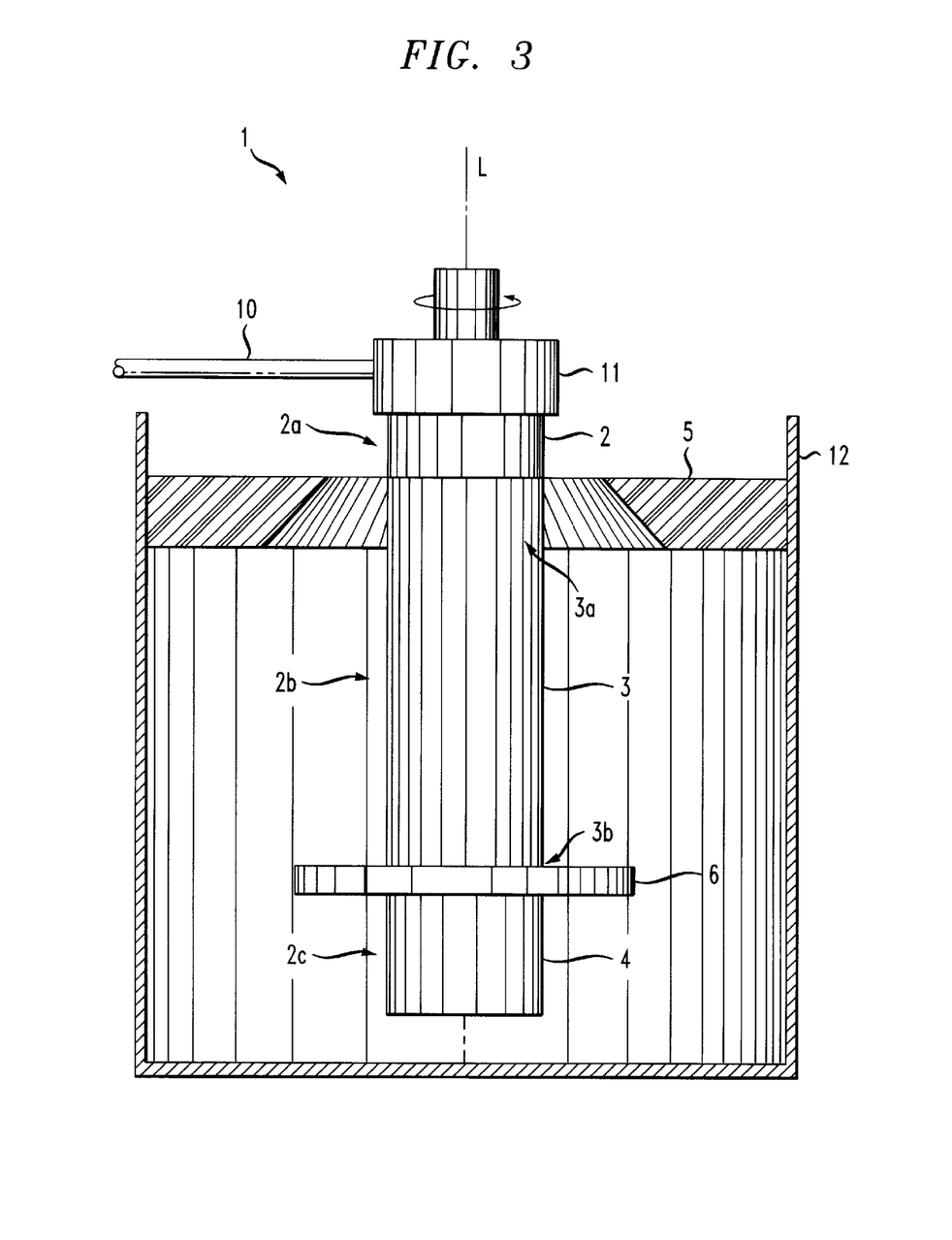
FIG. 3 is a schematic representation of another embodiment of the present invention.

As shown in FIG. 3, the L-Cell can be adapted for suspension in an electroplating solution which may be in its own container 12 or in a plating tank (not shown). An arm 10 supports L-Cell 1 for suspension in an electrolyte and includes a drive 11, which enables rotation of the cylindrical body 2 about its longitudinal axis L. The drive 11 may be any suitable device, such as a belt drive or a motor, which can provide rotation of cylindrical body 2 about its longitudinal axis L at a desired rate of rotation.

Figure 4:
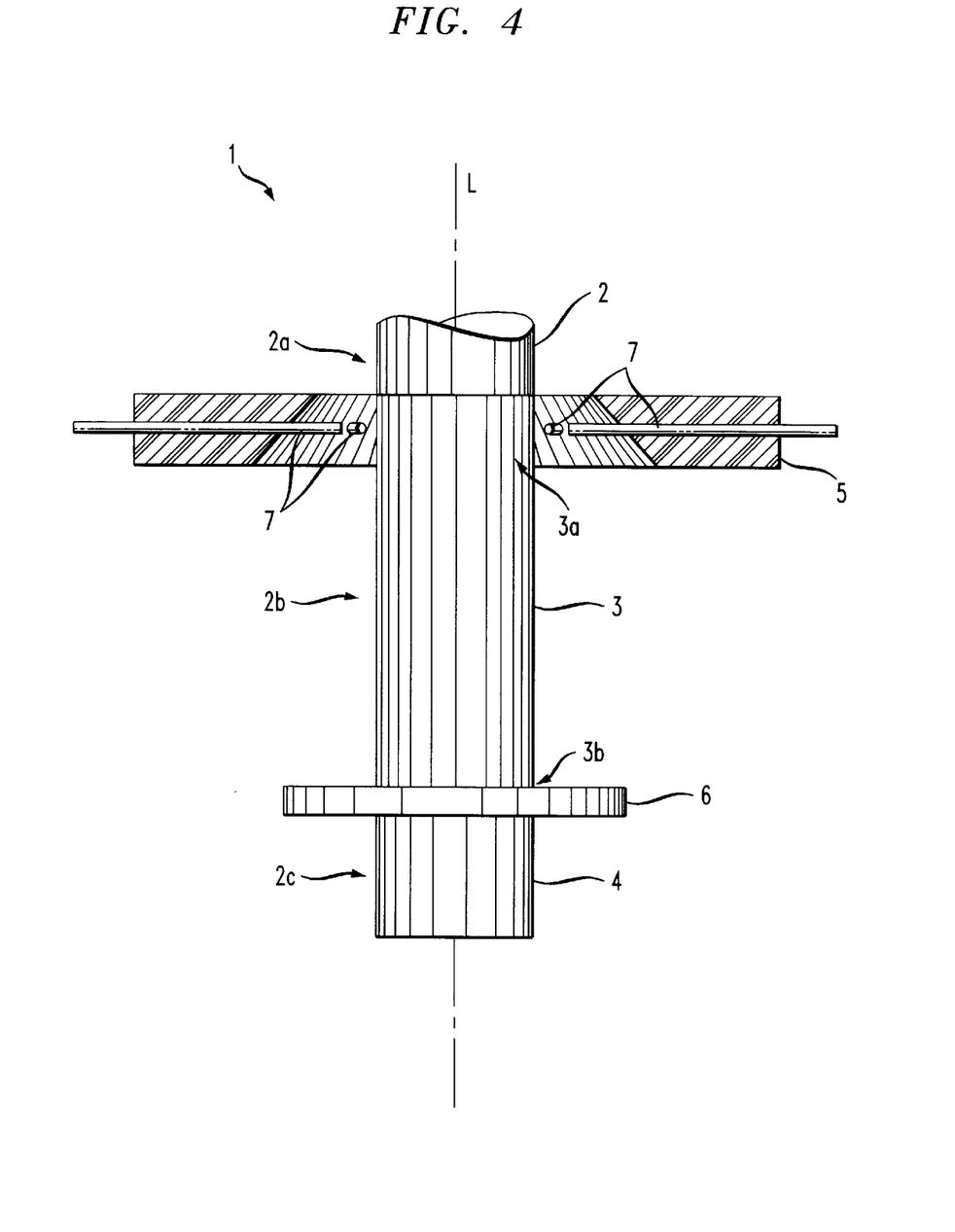
FIG. 4 is a schematic representation of another embodiment of the present invention.
Figure 5:
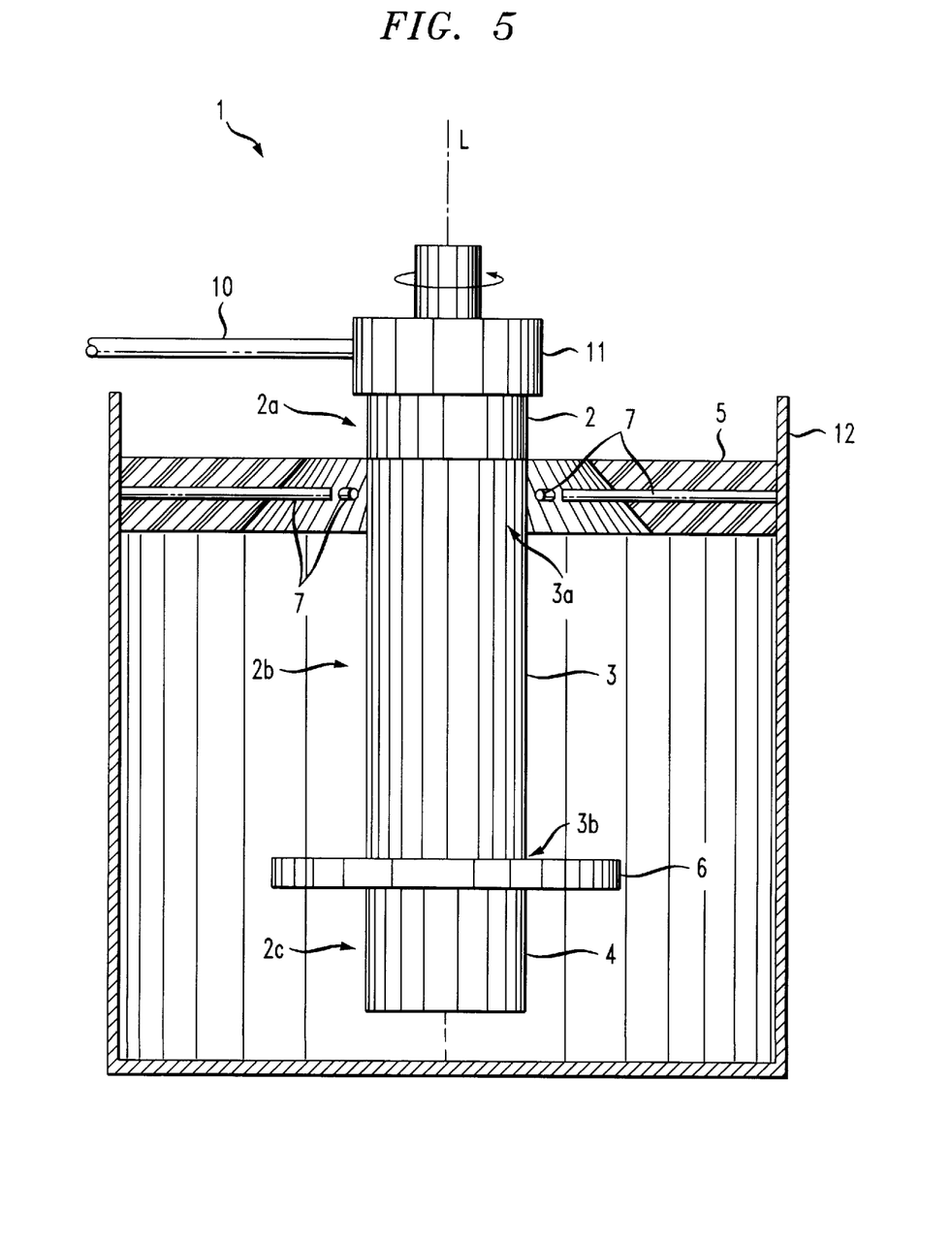
FIG. 5 is a schematic representation of another embodiment of the present invention.

In alternate embodiments shown in FIGS. 4 and 5 conical shield 5 includes one or more cylindrical screws 7 positioned radially around and within the conical shield 5. Cylindrical screws 7 are preferably ⅛" in diameter and extend from conical shield 5 toward cylindrical body 2. Cylindrical screws 7 are provided to prevent the formation of a vortex in the electroplating solution around the cylindrical body 2 while the cylindrical body 2 is rotating. The creation of a vortex lowers the level of the electroplating solution around cylindrical body 2 negatively affecting performance of the apparatus. Any apparatus commonly known or used in the art may be used with or in place of cylindrical screws 7 to eliminate the formation of a vortex within the electroplating solution.

Figure 6:
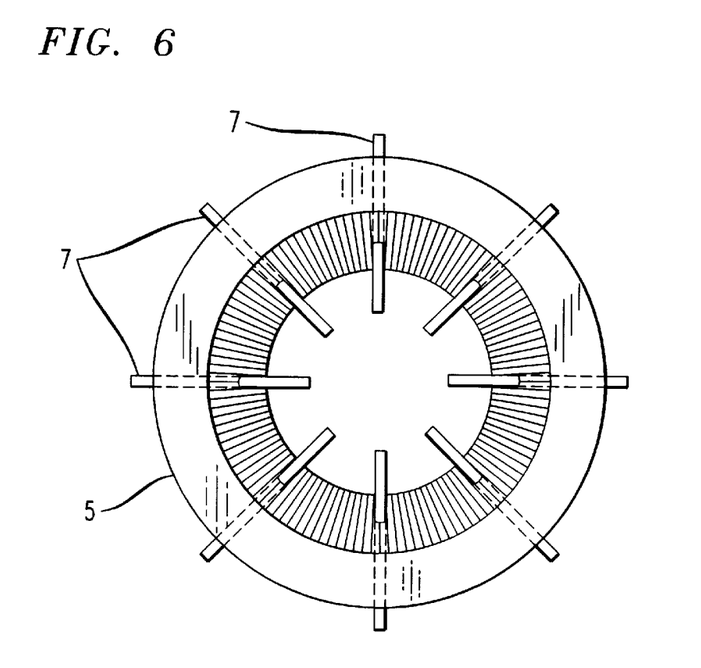
FIG. 6 is a bottom view of the conical shield with cylindrical screws of the present invention.
Figure 7:
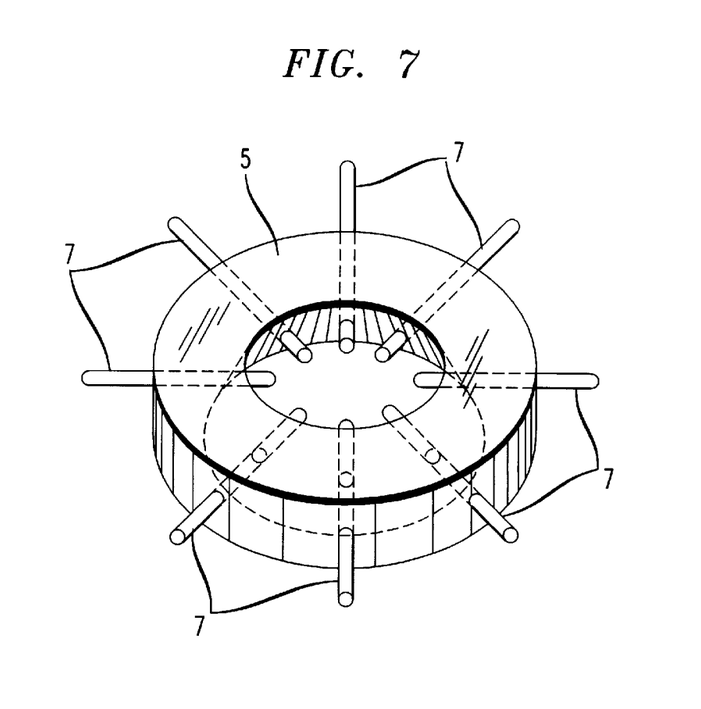
FIG. 7 is a perspective view of the conical shield with cylindrical screws of the present invention.

FIGS. 6 and 7 respectively show a bottom view and a perspective view of an embodiment of the conical shield 5 with the cylindrical screws 7.

Plating experiments were conducted to evaluate actual operation of the L-Cell and to verify basic design parameters. Table 1 illustrates some of the preferred basic L-Cell parameters.

TABLE 1

| Parameter | Dimensions (mm) |
| --- | --- |
| Panel length, cathode | 75 |
| Insulating disk baffle thickness | 5 |
| Anode | 25 |
| Total cell depth | 110 |
| Conical shield depth | 20 |
| Conical shield maximum distance | 20 |
| Conical shield minimum distance | 5 |
| Insulating disk baffle protrusion | 15 |

In evaluating the performance of the L-Cell in practical conditions, we determined the effect of variation in the cell depth and in the side-wall distance on the current distribution curve. We also determined what change if any would be needed to reduce the effect of either of these two variables. Three common types of commercially available containers were selected—600 ml, 1000 ml, and 1500 ml. As a severe condition an open container like tank was also tested. The parameters of tests run with both the bottom distance variation and wall distance variation are shown in Table 2. Container/tank refers to the volume of the electrolyte container. The diameter refers to the diameter of the test container. The bottom distance refers to the distance from the end of the anode furthest from the cathode to the bottom wall of the test container. Total depth refers to the total depth of the test container. The wall distance refers to the distance from the outer surface of the cathode to the wall of the container.

TABLE 2

| Container/Tank | Diameter (mm) | Bottom distance (mm) | Total depth (mm) | Wall distance (mm) |
| --- | --- | --- | --- | --- |
| 600 ml | 85 | 5 | 110 | 33 |
| 1000 ml | 105 | 20 | 125 | 43 |
| 1500 ml | 115 | 30 | 135 | 47 |
| open/tank | | 100 | 205 | 100 |

Figure 8A:
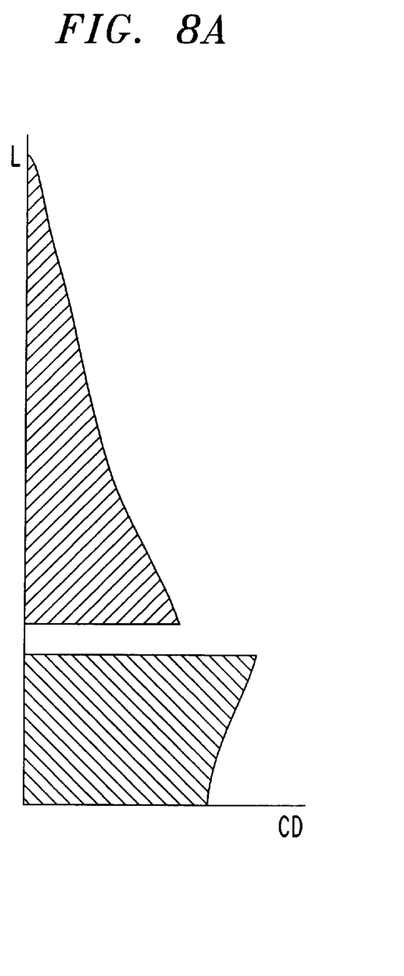
FIG. 8A is a plot showing the effect of bottom distance on current density distribution.
Figure 8B:
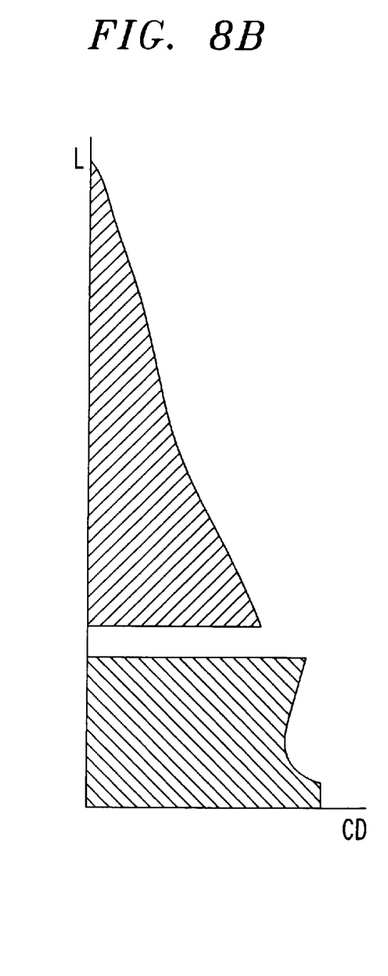
FIG. 8B is a comparative plot showing the effect of bottom distance on current density distribution.
Figure 9A:
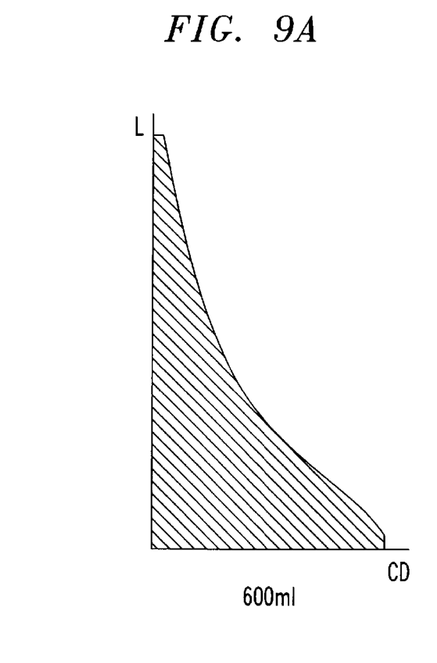
FIG. 9A is a plot showing the effect of side-wall distance on current density distribution.
Figure 9B:
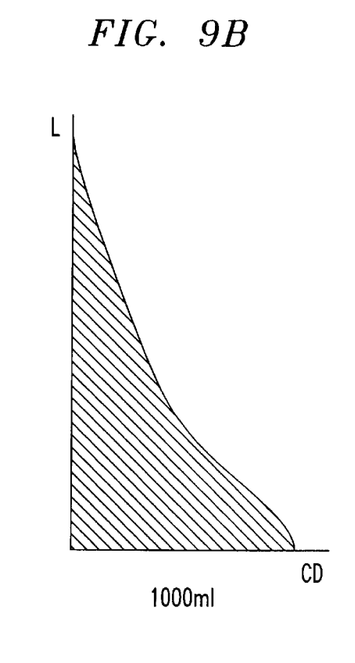
FIG. 9B is a comparative plot showing the effect of side-wall distance on current density distribution.
Figure 9C:
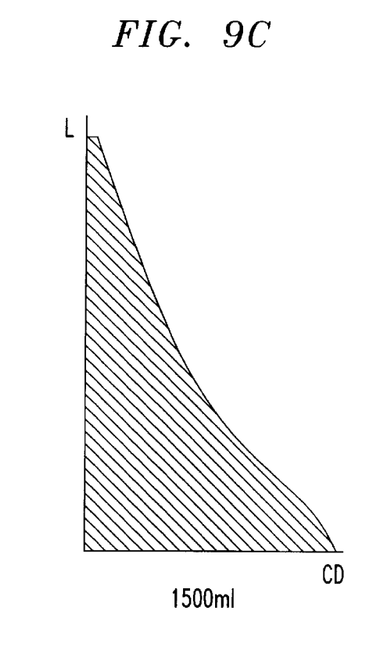
FIG. 9C is a comparative plot showing the effect of side-wall distance on current density distribution.
Figure 9D:
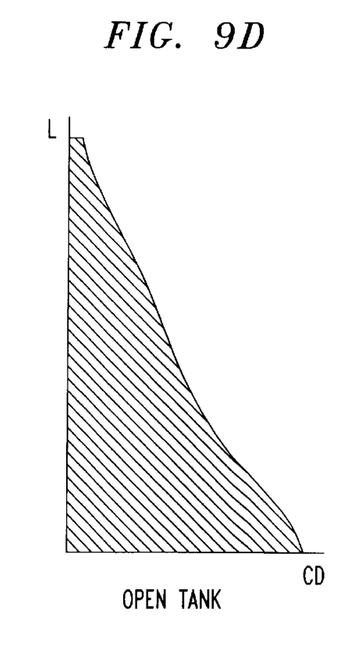
FIG. 9D is a comparative plot showing the effect of side-wall distance on current density distribution.

FIGS. 8A & 8B show the current density (CD) distribution over the length (L) of the cylindrical body 2 in comparative tests having a minimum, 5 mm, and a maximum, 100 mm, distance from the bottom. Both tests were run with a distance of 33 mm from the side-wall (similar results were found for tests performed with wider side-wall distances). As can be seen from the results in FIGS. 8A and 8B, there is no observable effect of the cell bottom distance from the L-Cell on the current distribution.

FIGS. 9A–D shows the current density (CD) distribution over the length (L) of cathode 3 of comparative tests on the effect of side-wall distance. The tests were performed at a fixed bottom distance of 5 mm. As can be seen in FIGS. 9A–D, the effect of side-wall distance is minimal (especially from the 1000 ml container to the open tank). However, linearity of the current distribution is gradually approached as the wall distance is increased. It is therefore preferable that the distance from outer surface of cathode to inner surface of the container is greater than about 43 mm.

Figure 10:
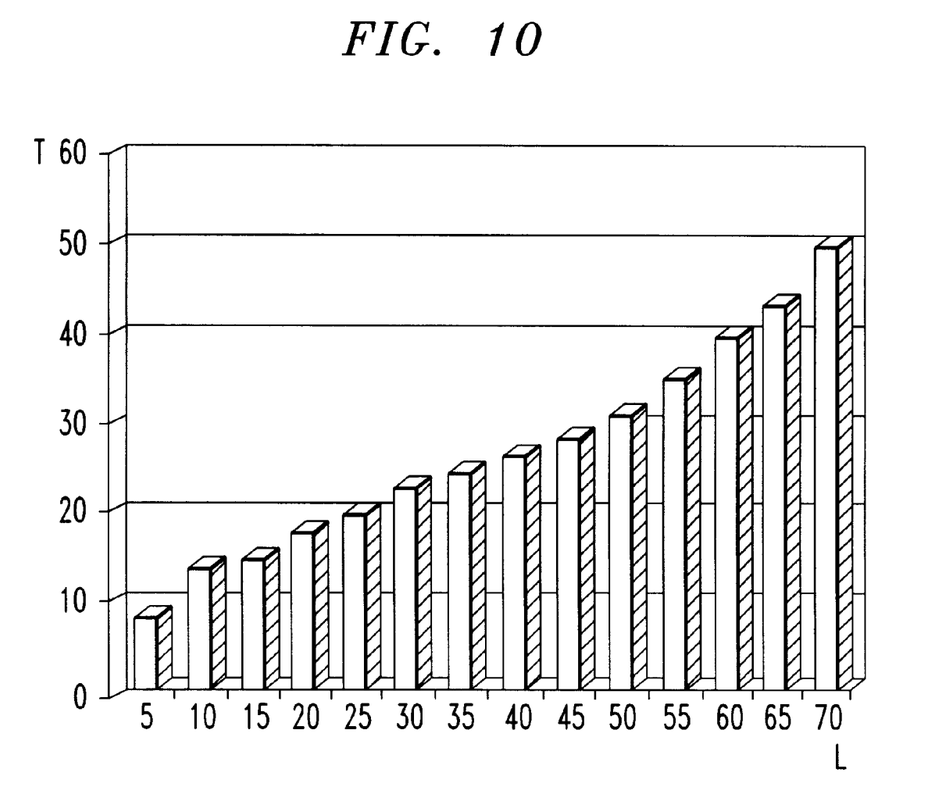
FIG. 10 is a chart showing Nickel deposit thickness as a function of panel length.

A test was also performed using a standard Nickel sulfamate solution. The test was run using a 1000 ml container at 2000 RPM, 2.5 A for 20 seconds. FIG. 10 shows the readings of the Nickel deposit thickness (T) as a function of length (L) of a test panel. In this test, the deposit thickness variation along the test panel length followed a substantially linear slope of 50 microinches over a 75 millimeter length of test panel.

An example showing use of the method and apparatus of the present invention will now be described. The L-Cell was used for testing a typical Nickel sulfamate high speed plating solution. The plating solution was heated to 60° C. A copper L-Cell test panel was attached to the cathode of the L-Cell and electrolytically cleaned in a phosphate-based alkaline cleaner. The test panel is preferably a flexible metal panel removably secured to an outer surface of the cathode. A current of 5 amps (100 amps per square foot) was applied to the L-Cell and the desired rate of rotation of the cylindrical body was set to 2500 revolutions per minute without the initiation of rotation of the cylindrical body. The L-Cell was then immersed in the Nickel solution such that approximately 50% of the conical shield was immersed in the electroplating solution. Rotation of the cylindrical body was then initiated. The nickel plating was allowed to continue for three minutes, at which time the L-Cell was removed from the electroplating solution. The test panel was removed from the L-Cell and rinsed with deionized water. The test panel was then rinsed in methanol and air dried with a compressed air jet. The test panel was then evaluated for thickness distribution using an X-ray fluorescence instrument known in the art and specifically designed to determine the thickness of metals. The instrument had been calibrated for nickel over copper.

These findings have important practical implications. The L-Cell, incorporating the conical shield and the disk baffle, can be utilized in both the laboratory and in the shop area for quality control and maintenance. Testing with the L-Cell can be performed in smaller containers and in an open tank without significant variation in the current distribution.

Although the present invention has been described in its preferred embodiments with reference to the accompanying drawing, it can be readily understood that the present invention is not limited to the specific details, representative devices and examples shown and described. Accordingly, various changes and modifications may be made without departing from the spirit and scope of the general inventive concept as defined by the appended claims and their equivalents.

We claim:

1. An instrument for measuring throwing power of an electrolyte, comprising:

a cylindrical body adapted for rotation about a longitudinal axis thereof, said cylindrical body having a upper end portion, a central portion and a lower end portion;

a cylindrical cathode arranged coaxially about said central portion of said cylindrical body, said cathode having a upper end portion, a lower end portion and an outer surface;

an anode coaxially positioned at said lower end portion of said cylindrical body;

a conical shield coaxially arranged around said upper end portion of said cathode; and an annular disk-baffle coaxially arranged around said lower end portion of said cathode, wherein said conical shield and said disk-baffle provide a substantially linear current distribution over said cathode.

2. The instrument defined in claim 1, wherein dimensions of said disk baffle and said conical shield are selected to provide a substantially linear current density distribution over said cathode.

3. The instrument defined in claim 1, wherein said conical shield includes one or more cylindrical screws arranged radially about said conical shield and extending inward toward said cylindrical body.

4. The instrument defined in claim 1, further comprising a container, a support arm for supporting said cylindrical body within said container, and a drive means for rotating said cylindrical body about its longitudinal axis at a desired rate of rotation.

5. The instrument defined in claim 1, wherein said cathode further comprises a flexible metal panel removably secured to said outer surface of said cathode.

6. The instrument in claim 1, wherein said cylindrical body has a diameter of about 0.75 inch.

7. The instrument defined in claim 3, wherein the distance from said outer surface of said cathode to an inner surface of said container is greater than about 43 mm.

8. A method for testing an electroplating solution comprising:

attaching a test panel to the cathode of the instrument defined in claim 1;

applying a current to said instrument;

immersing said instrument in an electroplating solution such that approximately 50% of said conical shield is immersed;

rotating said cylindrical body;

removing said instrument from said electroplating solution, and evaluating said test panel for thickness distribution.

* * * * *